United States Patent [19]

Naraghi

[11] Plant 4,845

[45] May 11, 1982

[54] ALMOND TREE

[76] Inventor: Hashem Naraghi, 17428 Keyes Rd., Denair, Calif. 95316

[21] Appl. No.: 161,221

[22] Filed: Jun. 19, 1980

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is large, open, vigorous, spreading, abundantly foliated with large, lanceolate leaves having a finely serrate margin, blooms heavily and prolonged with white pink-centered flowers, and a regular bearer with very heavy production of large, well-distributed nuts having a large kernel.

1 Drawing Figure

BACKGROUND OF THE VARIETY

1. Field of the Discovery

The present new and distinct variety of almond tree is embraced by Class 30, Plants, of the U.S. Patent Office Manual of Classification.

2. Prior Varieties

Among the existent varieties of almond tree which are known to me, and mentioned herein, are Nonpareil and Mission (both unpatented), Merced (U.S. Plant Pat. No. 1,730), Carmel (U.S. Plant Pat. No. 2,641), and Naraghi I (U.S. Plant Pat. No. 4,466).

ORIGIN OF THE VARIETY

The present variety of almond tree was discovered by me growing as a sport limb in my orchard of almond trees (Nonpareil, Mission, and Merced) located near Denair, Stanislaus County, Calif.

Upon discovery of such sport limb, and recognizing the apparent commercial value of the variety, asexual reproduction of the variety was undertaken.

ASEXUAL REPRODUCTION OF THE VARIETY

The present variety of almond tree was asexually reproduced, on my behalf and by a commercial nursery, by grafting and budding, and such asexual reproduction—in maturity—ran true to the original tree in all respects.

SUMMARY OF THE VARIETY

The herein-claimed variety of almond tree is large, open, vigorous, spreading, abundantly foliated with large, lanceolate leaves having a finely serrate margin, blooms heavily and prolonged with white pink-centered flowers, and a regular bearer with very heavy production of large, well-distributed nuts having a large kernel.

The herein-claimed variety of almond tree, while generally similar to the Nonpareil, is particularly distinctively characterized, in comparison, by a prolonged blooming period spanning as much as three weeks; by being an effective pollenizer for the Nonpareil; and by productivity substantially greater (up to 70%) than the Nonpareil.

BRIEF DESCRIPTION OF THE DRAWING

The drawing is an illustration, by photographic reproduction in color, of a twig with leaves and nuts, a nut in hull, and—separately—nuts out of hull, and kernels out of shell, one kernel being partially cut away to expose the meat.

DESCRIPTION OF THE VARIETY

The botanical details of this new and distinct variety of almond tree—with color definitions (except those in common color terms) referenced to Maerz and Paul Dictionary of Color (First Edition—1930)—are as follows:

Tree:
- *Density.*—Open.
- *Size.*—Large.
- *Vigor.*—Vigorous.

Trunk:
- *Form.*—Stocky.
- *Texture.*—Medium.

Branches:
- *Form.*—Medium.
- *Texture.*—Medium.
- *Branching habit.*—Spreading.
- *Color.*—New wood: green. Mature wood: brown.

Foliage:
- *Quantity.*—Abundant.

Leaves:
- *Size.*—Large. Average length — 3". Average width — 1".
- *Shape.*—Lanceolate.
- *Thickness.*—Thin.
- *Texture.*—Smooth.
- *Margin.*—Finely serrate.
- *Petiole.*—Long. Medium thickness.
- *Glands.*—Average number — 2. Alternate. Positioned on petiole.
- *Color.*—Top side — medium green (22-I-8). Under side — lighter green (22-G-8).

Bloom:
- *Amount of bloom.*—Heavy.
- *Color.*—White, pink-centered.
- *Blooming period.*—Prolonged — as much as three weeks. Date of first bloom: medium; on or about March 1st; substantially with Nonpareil.

Crop:
- *Bearing.*—Regular bearer.
- *Productivity.*—Very heavy. 70% more abundant than Nonpareil.
- *Distribution of nuts on tree.*—Well distributed.

*Harvest period.*—September 1st. Early, as compared with Merced and Carmel. About with Nonpareil.

*Tenacity.*—Hangs well on tree. Easy to harvest. Easy to hull.

Hull:

*Outer surface.*—Smooth.

*Pits.*—Pitted.

*Form.*—Regular.

*Thickness.*—Thick.

*Flesh.*—Fleshy.

*Suture.*—Ridged.

*Color.*—Light green (21-I-6) shading darker to Cress Green (22-K-6), with silvery sheen.

*Dehiscence.*—Opens freely.

*Splitting.*—Along suture.

Nut:

*Size.*—Large. Average length — 1½″. Average width — ⅞″. Average thickness — ⅝″. Average weight — 3.2 grams.

*Form.*—Length/width: ovate. Width/thickness: plump.

*Shell.*—Paper. Outer shell: crumbling. Inner shell: soft. Well sealed.

*Color.*—Desert Brown (12-I-7).

*Pits.*—Small. Few. Round.

*Base.*—Dorsally oblique.

*Stem scar.*—Small. Acute.

*Apex.*—Acute. Prolonged at tip.

*Wing.*—Narrow. Thin. Tapered toward base.

*Inner surface.*—Light.

*Ventral streak.*—Dark. Narrow. Long. Point acute.

*Percentage of kernel to nut.*—62%-68%.

Kernel:

*Size.*—Large. Average length — 1″. Average width — ½″. Average thickness — ⅜″.

*Form.*—Length/width: elongated. Wedge. Width/thickness: plump.

*Base.*—Square.

*Stem scar.*—Small. Acute.

*Apex.*—Acute. Sharp. Blunt. Tip recurved.

*Texture.*—Smooth.

*Pellicle.*—Thin.

*Pubescence.*—Veined.

*Color.*—Buckthorn Brown (13-L-8).

*Number of doubles.*—None.

*Defective kernels.*—None observed.

*Flavor.*—Sweet.

*Quality.*—Very good.

Resistance to insects and diseases: No unusual susceptibilities noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, having general resemblance to the Nonpareil, but distinctively characterized by a prolonged blooming period spanning as much as three weeks; by being an effective pollenizer for the Nonpareil; and by productivity substantially greater than the Nonpareil.

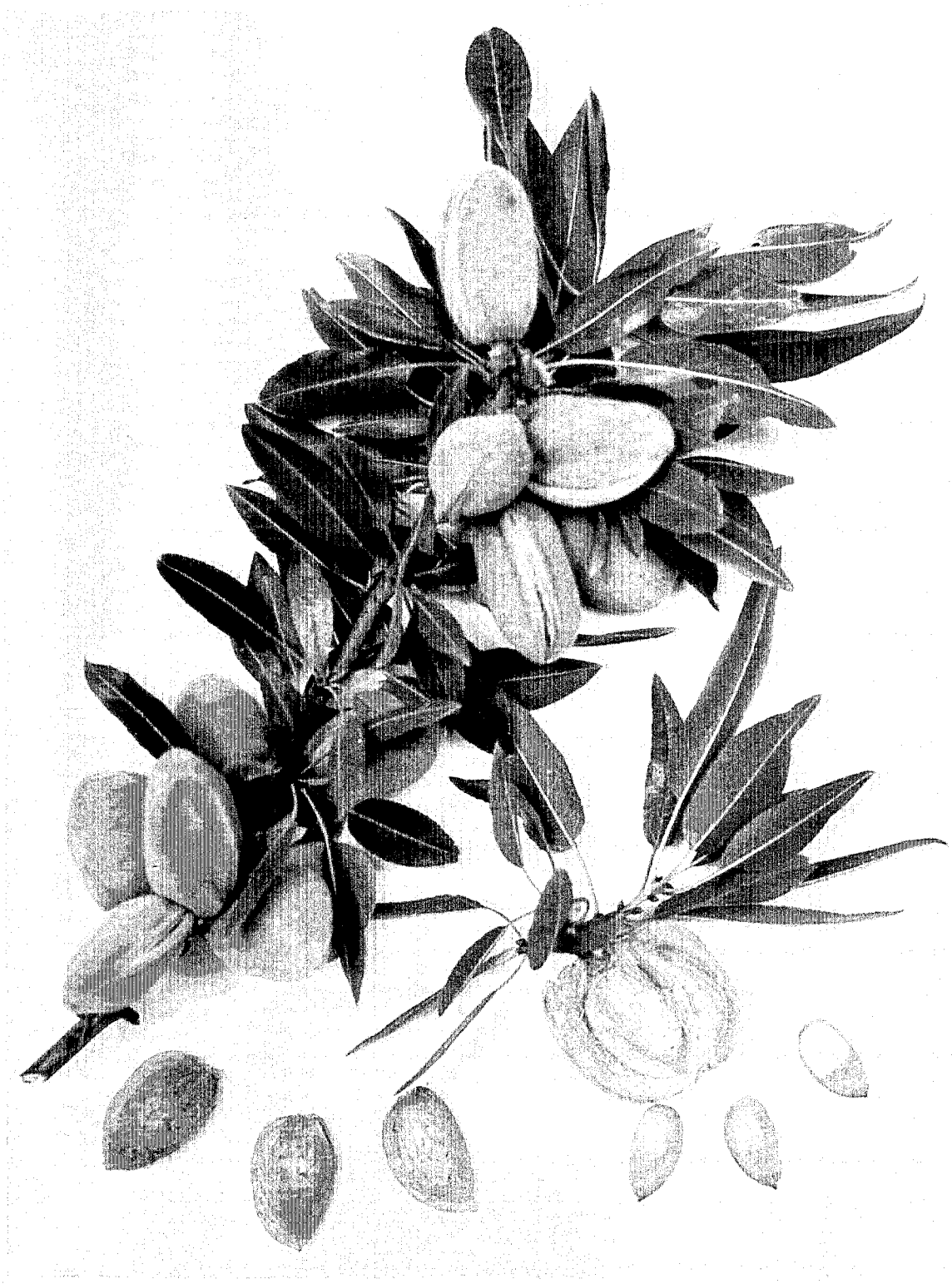

* * * * *